United States Patent [19]

Behl et al.

[11] 4,419,091
[45] Dec. 6, 1983

[54] METALIZED MEDICAL TREATMENT ELECTRODE WITH INSULATED EDGE

[75] Inventors: Robert S. Behl, Fairport; Franklin H. Ellis, Rochester, both of N.Y.

[73] Assignee: Sybron Corporation, Rochester, N.Y.

[21] Appl. No.: 233,899

[22] Filed: Feb. 12, 1981

[51] Int. Cl.³ .............................................. A61N 1/30
[52] U.S. Cl. ...................................... 604/20; 128/798; 128/803
[58] Field of Search ............................. 128/639–641, 128/644, 783, 798, 802, 803, 207.21; 604/20

[56] References Cited

U.S. PATENT DOCUMENTS

| | | | |
|---|---|---|---|
| 1,989,282 | 1/1935 | Kimble et al. | 128/798 |
| 3,542,010 | 11/1970 | Love | 128/644 |
| 3,662,757 | 5/1972 | Blackett | 128/798 |
| 4,092,985 | 6/1978 | Kaufman | 128/798 X |

FOREIGN PATENT DOCUMENTS 675494 12/1963 Canada ................................. 128/798

*Primary Examiner*—Lee S. Cohen
*Attorney, Agent, or Firm*—Robert A. Gerlach; Robert J. Bird; J. Stephen Yeo

[57] ABSTRACT

An ion treatment electrode has a porous polymer substrate with a conductive coating. A non-conductive solution impervious border is provided by applying to adjacent substrate, sufficient heat and pressure to melt the polymer and disrupt the conductive coating.

2 Claims, 5 Drawing Figures

U.S. Patent     Dec. 6, 1983     4,419,091
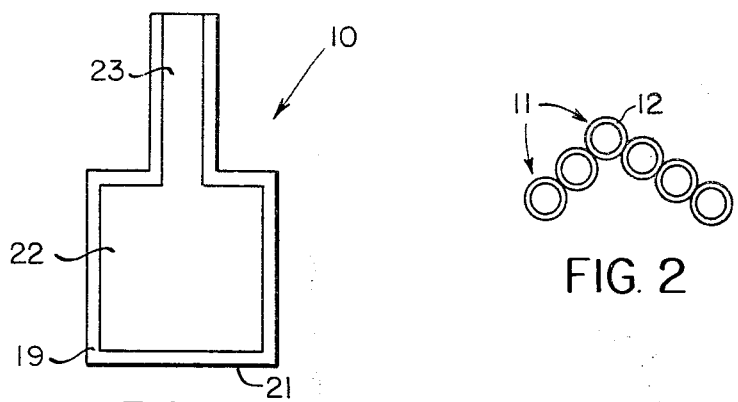
FIG. 1
FIG. 2
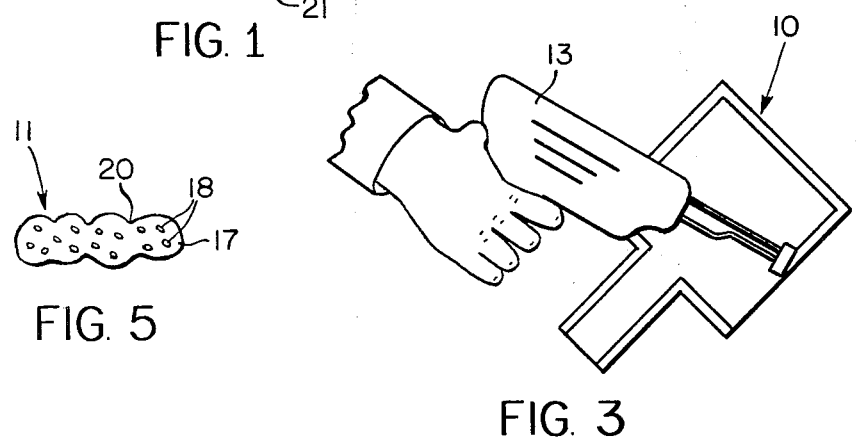
FIG. 5
FIG. 3
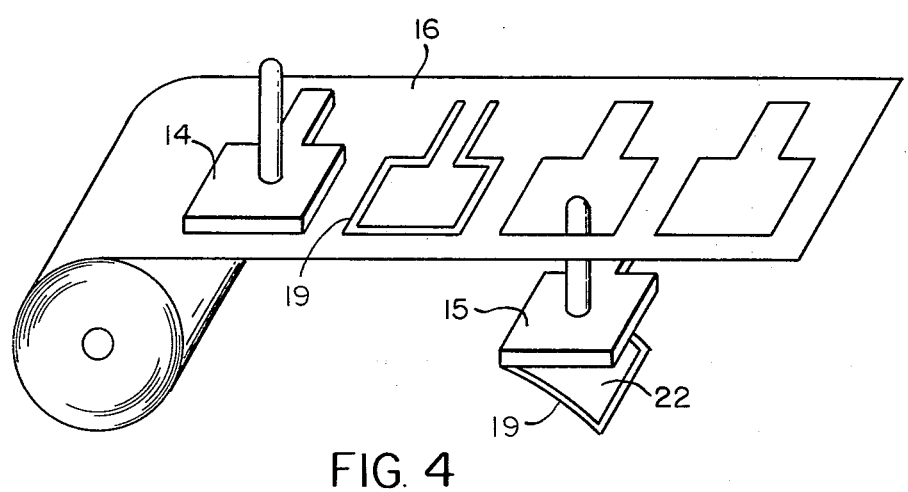
FIG. 4

METALIZED MEDICAL TREATMENT ELECTRODE WITH INSULATED EDGE

BACKGROUND OF THE INVENTION

This invention pertains to medical electrodes, and more particularly, is concerned with electrodes for use in ion therapy. Many types of wounds or lesions may be treated through use of a porous metalized treatment electrode energized by a constant current generator. This treatment electrode is typically in the form of a film of active metallic material (i.e. silver) which is plated or otherwise deposited over a porous synthetic fiber substrate.

Before use, the treatment electrode size is selected to approximate the shape of the patient's wound or lesion. The electrode is held by gauze or the like so as to be in contact with the patient's tissue (A return electrode is placed elsewhere on the patient). A tab extends from the electrode to provide electrical contact to the current generator. The patient completes an electric circuit formed by the current source, the treatment electrode as an anode, and the return electrode as a cathode. Current flow from the surface of the treatment electrode causes migration of metal ions from the metallic coating in the general direction of the return electrode.

Two problems arise during the treatment if the electrode is merely cut to the appropriate size by the manufacturer or by the user.

The first problem is due to loose or protruding fibers from a cut or sheared edge which can form a more intimate contact with the tissue than does the balance of the electrode. This contact provides a lower resistance path with corresponding preferential current and ion flow away from the central portion of the lesion.

The second problem occurs when a moderately conductive solution, such as normal saline, is used to soak the electrode and surrounding tissue for improving conduction and quantity of ion flow. A radial flow of current from the periphery of the infection site may occur. In both of these situations the diversion of current and ions away from the treatment site has the undesirable effect of reducing the desired ion concentration in the treatment area. Accordingly, it is the primary object of the invention to provide an electrode within a non-conductive, solution impervious border and a method for making the same.

BRIEF DESCRIPTION OF THE DRAWINGS

FIG. 1 is a view of a treatment electrode made according to the invention;

FIG. 2 is a cross sectional view of coated electrode fibers prior to melting;

FIG. 3 shows the fabrication of an electrode border by use of a hand tool to apply heat and pressure sufficient to cause melting; and FIG. 4 illustrates the use of a heated stamp and a die to form a border of melted fibers and cut an electrode from a web;

FIG. 5 is a cross sectional view of fused fibers within a border after melting.

DESCRIPTION OF THE INVENTION

We have found that the provision of electrically non-conductive borders about the periphery of an ion treatment electrode solves several problems found in the prior art.

An ion treatment electrode 10, seen in FIG. 1, is manufactured with a flexible porous substrate or fabric preferably made of woven or unwoven solid synthetic polymer fibers, such as nylon or rayon. As seen in FIG. 2, the fibers 11 are covered with a thin conductive metallic layer 12 preferably of silver, which may be deposited over sublayers of other conductive material such as tin. The drawing is not to scale as the total cross sectional area of the conductive layers has been found to be usually one thousandth or less of the cross sectional area of a fiber.

In accordance with the invention, the electrode edge is sealed by a non-conductive border either before or after the electrode 10 is cut from a larger piece of material. A hand held heat tool 13, such as illustrated in FIG. 3, can be utilized to fabricate the border, after the electrode is cut to shape.

The preferred method, however, is illustrated by FIG. 4. A heated stamp 14, or equivalent means of rapidly applying heat and pressure is used to melt the adjacent polymer substrate and fuse the individual fibers together. As an additional feature of the invention a die 15, punch, or other cutting means may be combined with heated stamp 14 for simultaneously or sequentially cutting the electrode from a web 16 of surrounding material, while retaining the sealed area as the electrode border. A sequential operation of application of the heated stamp 14 followed by cutting with die 15 is represented in FIG. 4.

FIG. 5, shows that the applied heat and pressure melts the polymer fiber 17 and disrupts the conductive coating by diffusing and encapsulating the conductive particles 18. The polymer itself, is an effective electrical insulator, and therefore provides a border 19 with high electrical resistance which prevents measurable current at physiologic voltage levels. The molten polymer fibers are also fused together at their junctions 20 at the edge of the fabric substrate. This provides a smooth non-conductive edge 21 on the electrode as best seen in FIG. 1. The bonded fibers are impervious to a conductive solution such as saline. The center area 22 of the electrode, remains conductive and porous.

In order to make electrical contact to the electrode a conductor tail or tab 23 may extend from an edge of the electrode. Preferably tab 23 and the rest of the electrode are one piece and cut out of the web at the same time. The insulative border is arranged not to cross the tab, but to extend along the edge of the tab.

We claim:

1. A flexible porous electrode for ion therapy comprising a substrate of polymer fibers, each of such fibers coated with a thin layer of conductive material to form a conductive mass, said substrate characterized by:
   a peripheral border in which said fibers are fused into a liquid-impervious and non-conductive mat, whereby conductive solution and conductive fibers are generally contained within said border, and ion concentration and current flow are thereby confined to the area within the periphery defined by said border, and
   said substrate including a tab portion through which said conductive fibers are adapted for electrical connection to a conductor.

2. The device as defined in claim 1 in which said electrode is formed as a one piece element.

* * * * *